US005138664A

United States Patent [19]

Kimura et al.

[11] Patent Number: 5,138,664

[45] Date of Patent: Aug. 11, 1992

[54] NOISE REDUCING DEVICE

[75] Inventors: Akira Kimura, Kanagawa; Tooru Sasaki; Nobuo Kobayashi, both of Tokyo, all of Japan

[73] Assignee: Sony Corporation, Tokyo, Japan

[21] Appl. No.: 493,432

[22] Filed: Mar. 14, 1990

[30] Foreign Application Priority Data

| | | | |
|---|---|---|---|
| Mar. 25, 1989 | [JP] | Japan | 1-75277 |
| Mar. 25, 1989 | [JP] | Japan | 1075276 |
| Mar. 29, 1989 | [JP] | Japan | 1-74833 |

[51] Int. Cl.[5] .......... A61F 11/02; G10K 11/16

[52] U.S. Cl. .......... 381/72; 381/71

[58] Field of Search .......... 381/71, 72, 94, 68.6

[56] References Cited

U.S. PATENT DOCUMENTS

| | | | |
|---|---|---|---|
| 4,455,675 | 6/1984 | Bose et al. | 381/71 |
| 4,953,217 | 8/1990 | Twiney et al. | 381/72 |
| 4,985,925 | 1/1991 | Langberg et al. | 381/72 |
| 5,001,763 | 3/1991 | Moseley | 381/72 |

FOREIGN PATENT DOCUMENTS

| | | |
|---|---|---|
| 1000931 | 5/1989 | Belgium . |
| 2601661 | 7/1977 | Fed. Rep. of Germany . |
| 2160070 | 12/1985 | United Kingdom . |
| 2172769 | 9/1986 | United Kingdom . |

OTHER PUBLICATIONS

U.S. Statutory Inventin Registration Publiation H417 (Mies) Jan. 5, 1988.

*Primary Examiner*—Forester W. Isen
*Attorney, Agent, or Firm*—Lewis H. Eslinger; Jay H. Maioli

[57] ABSTRACT

This invention is concerned with a device for reducing the external noise reaching the ear in extremely noisy places such as in the vehicle or construction sites. According to the present invention, the external noise in picked up by a microphone provided in the vicinity of an electro-acoustic transducer element, such as a headphone unit, provided in the vicinity of the wearer's ear, and the noise signal converted in this manner into electrical signals is produced as the acoustic signal by the electro-acoustic transducer element. The transfer characteristics and controlled in such a manner that the produced noise signal prove to be an acoustic signal which is of the same frequency spectrum and opposite in phase with respect to the external noise reaching the wearer's acoustic meatus from outside to reduce the external noise reaching the acoustic meatus.

8 Claims, 6 Drawing Sheets

NOISE REDUCING DEVICE

BACKGROUND OF THE INVENTION

1. Field of the Invention

This invention relates to a sound reducing device which may be conveniently employed under extremely noisy conditions, such as in a vehicle or on construction sites, for reducing the external noise.

2. Prior Art

Up to now, a so-called ear-applying type noise reducing device has been extensively known for use in operations in extremely noisy places. This ear-applying type noise reducing device is attached to the user's head so as to be pressed onto side head portions, with a headphone cup covering the ears, to reduce the noise from the environment, and is used so that the noise from the environment is not intruded via a gap between the headphone cup and the side head portions.

More specifically, the inside of the cockpit of a helicopter or an aircraft represents an extremely noisy environment with the engine noises or the like which render it difficult for the pilot to recognize the contents of communications with the control tower. Thus the pilot is obliged to attach the headphone cup to his side head portions to reduce the noises from the environment.

Also, when the user intends to hear the playback sounds from a portable sound reproducing device with a headphone device in extremely noisy surroundings, the sound volume need be raised to elevate the playback sound level higher than the noise from the environment.

In addition, when one talks over a public telephone, the voice of the called party cannot be heard in noisy places, so that one has to raise the voice as much as possible in order to talk over the telephone.

However, since it is necessary with the above mentioned ear-applying type noise reducing device to apply the headphone cup strongly to one's side head portions in order to reduce the external sound otherwise intruded via a space between the headphone cup and the side head portions, one may feel constricted at one's head. Moreover, the headphone device itself is increased in size and weight and hence cannot be used for an extended period of time.

On the other hand, if the playback sound level is raised to higher than the external noise in order to render the playback sound easy to hear, the playback sound is leaked from the interstices between the ear and the headphone device to inconvenience near-by persons or to cause disturbances to the auditory sense because of the excessively raised sound level.

Additionally, a telephone is needed wherein one may talk without being bothered by external noises.

Meanwhile, as a sound reducing device for reducing the external noises, there is known an active type headphone device such as is shown and described in the U.S. Pat. Nos. 4,455,675, 4,494,074 and 4,644,581.

With this active type headphone device, a negative feedback loop is used whereby the electrical signals converted from the external noises by a microphone unit are fed back in a reverse phase for reducing the noise in the vicinity of the headphone unit.

SUMMARY OF THE INVENTION

In view of the foregoing, it is an object of the present invention to provide a noise reducing device in which the external noises may be reduced without producing the sense of constrictions at one's head or without any adverse effects, such as oscillations, caused by the feedback loop.

It is another object of the present invention to provide an audible signal hearing device whereby external noises reaching the auditory meatus from outside may be reduced to enable the desired audio signals to be heard clearly.

According to the present invention, there is provided a sound reducing device comprising acoustic-electrical transducer means provided in the vicinity of the ear of a user wearing the sound reducing device and adapted for picking up the external noise, characteristics transmission means (control circuit and amplifier circuit) having predetermined phase and frequency characteristics and supplied with output signals from the acoustic-electrical transducer means, and electro-acoustic transducer means provided in the vicinity of the ear of the user wearing the sound reducing device and adapted for converting electrical output signals from the characteristics transmission means into acoustic signals, wherein the transfer characteristics from the acoustic-electrical transducer means to the electro-acoustic transducer means are in register with and opposite in phase with respect to the acoustic frequency characteristics of the external noise until reaching the user's acoustic meatus.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DESCRIPTION OF THE PREFERRED EMBODIMENTS

By referring to the accompanying drawings, certain preferred embodiments of the noise reducing device according to the present invention will be explained in detail.

Figure 1:
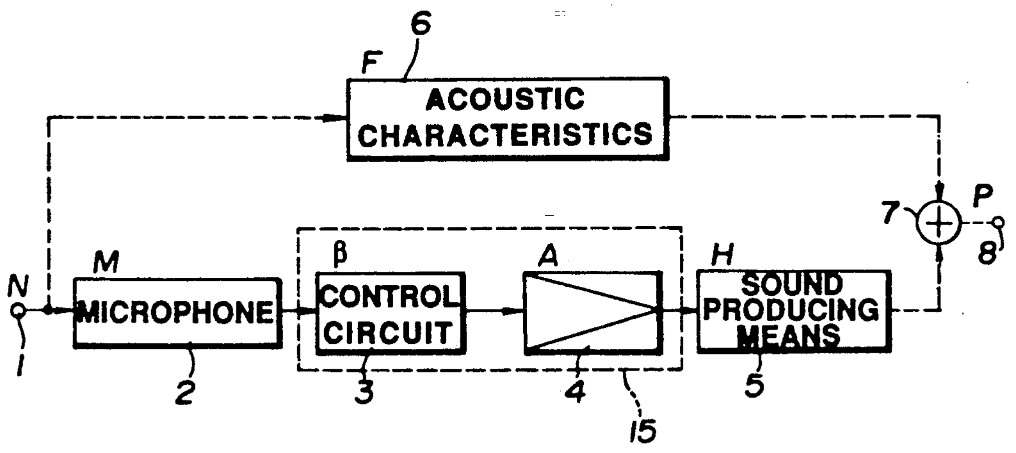
FIG. 1 is a block diagram showing the basic construction of the noise reducing device according to the present invention.

FIG. 1 is a schematic block diagram showing a basic arrangement of the noise reducing device according to the present invention.

With the noise reducing device shown in FIG. 1, external noises of the acoustic nature input to an acoustic input terminal 1 are supplied to a microphone 2 as acoustic-electrical transducer means for conversion into electrical signals. The output signals from the microphone 2 are supplied to characteristics transmitting means 15 consisting of a control circuit 3 and an amplifier 4. The control circuit 3 is matched to the acoustic frequency characteristics of the external noises reaching the ear, and is adapted to realize phase inversion by its frequency and phase characteristics. The output signals from control circuit 3 are supplied to sound producing means 5 after amplification by amplifier 4. The sound producing means 5 converts output electrical signals from amplifier 4 into acoustic signals. The produced acoustic signals are acoustically summed to acoustic signals from an acoustic characteristics block 6 by summation means 7 before being supplied to an acoustic output terminal 8 placed at the acoustic meatus. The acoustic characteristics block 6 demonstrates acoustic characteristics between the acoustic input terminal 1 and the acoustic output terminal 8. More specifically, the external noises pass by the user's ears or head or acoustically through the sound producing means 5, before reaching the user's acoustic meatus, so that the frequency spectrum of the external noises is changed. The acoustic block 6 represents the acoustic frequency characteristics of the external noises in the form of a acoustic circuit block.

Figure 2:
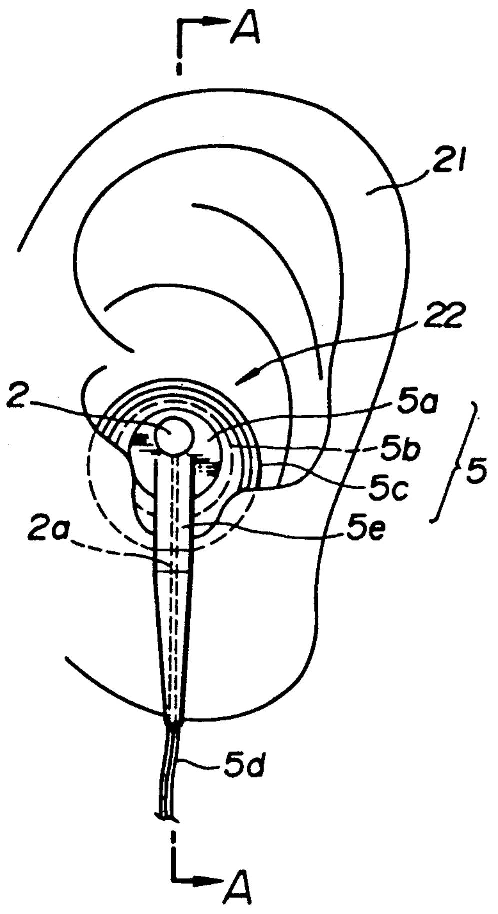
FIG. 2 is a rear view showing the state of use of the noise reducing device of FIG. 1 when applied to the inner type headphone device.
Figure 3:
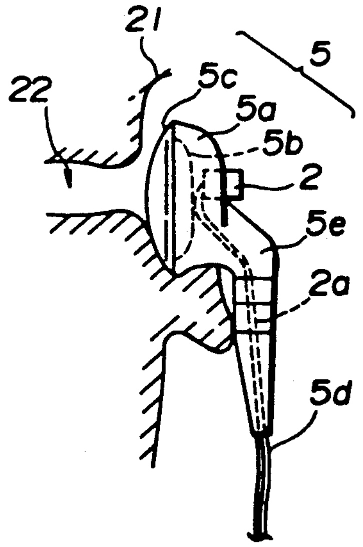
FIG. 3 is a sectional view taken along line A—A of FIG. 2.

FIG. 2 is an elevational view showing the state of use of a specific example of the noise reducing device when applied to a so-called inner ear type headphone device as described in the U.S. Pat. No. 4,736,435, and FIG. 3 is a cross-sectional view taken along line 3—3 of FIG. 2. In these figures, parts or components similar to those of FIG. 1 are indicated by the same numerals.

In FIGS. 2 and 3, the inner ear type headphone device is so constructed that a sound producer 5*b* and the microphone 2 are enclosed in a casing 5*a* of the sound producing means 5 so that the sound producer 5*b* and the microphone 2 are provided in the vicinity of the user's ear 21 when the headphone device is attached to the user's ear. The sound producer 5*b* is covered by a mesh 5*c*, while a lead 5*d* connected to the sound producer 5*b* and a lead 2*a* connected to the microphone 2 are taken out of a lead take-out unit 5*e*.

With the inner ear type headphone device attached to the ear 21, the external noises are collected by the microphone 2 provided in the vicinity of the acoustic meatus 22 and thereby converted into electrical signals, which are then input to the control circuit 3 shown in FIG. 1.

The control circuit 3 functions to reverse the phase of the output characteristics from microphone 2 with the above mentioned frequency characteristics. The output signals from the control circuit 3 are amplified by the amplifier having a predetermined gain and converted by the sound producing means 5 as the electro-acoustic converting means into acoustic signals which then are produced as an audible sound. The thus produced acoustic signals are acoustically summed at the summing means 7 to the external noises transmitted through the acoustic block 6. The acoustic signals produced by the sound producing means 5 are of the same frequency spectrum or register as but are reversed in phase with respect to the external noises reaching the acoustic meatus 22. The acoustic signals function to cancel the external noises reaching the acoustic meatus 22.

More specifically, with the sound pressure N at the acoustic input terminal 1, the transfer function $\beta$ of the control circuit 3, the transfer function A of the amplifier circuit 4, the transfer function H of the headphone unit 5 and with the transfer function F of the acoustic block 6, the sound pressure P at the acoustic output terminal 8 is given by $$P=(F+AHM\beta)N$$

wherein the transfer functions M, $\beta$, A, H and F are expressed in the frequency domain. For reducing the sound pressure P at the acoustic meatus 22 to zero, it suffices to reduce the coefficient of the sound pressure N of the external noises to zero. Hence it is sufficient if the transfer function $\beta$ of the control circuit 3 is such that $$F+AHM\beta=0$$

$$\therefore \beta=-F/AHM$$

Figure 4:
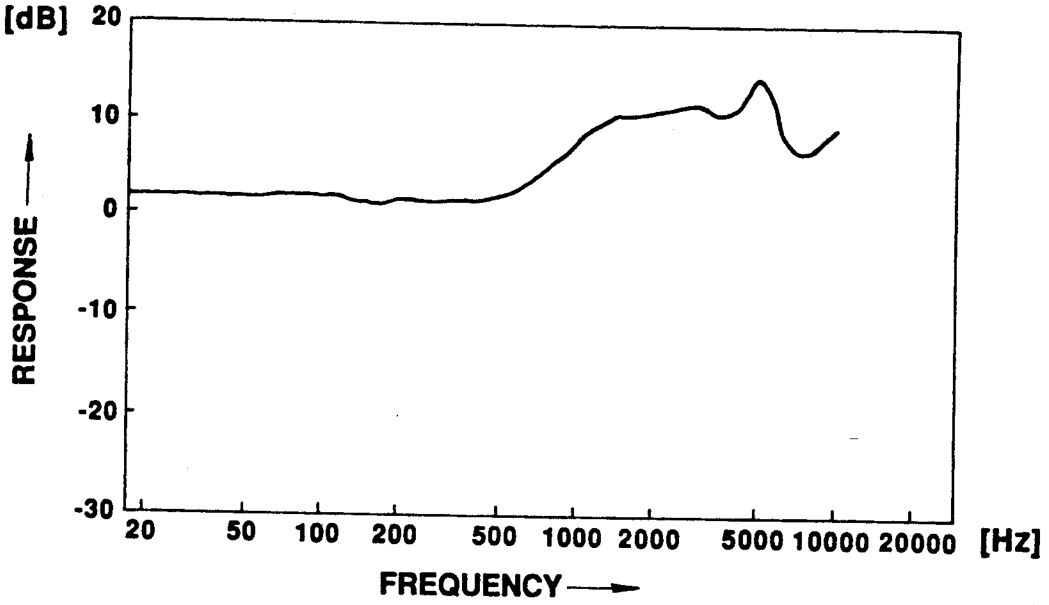
FIG. 4 is a chart showing output frequency characteristics of an acoustic characteristics block.
Figure 5:
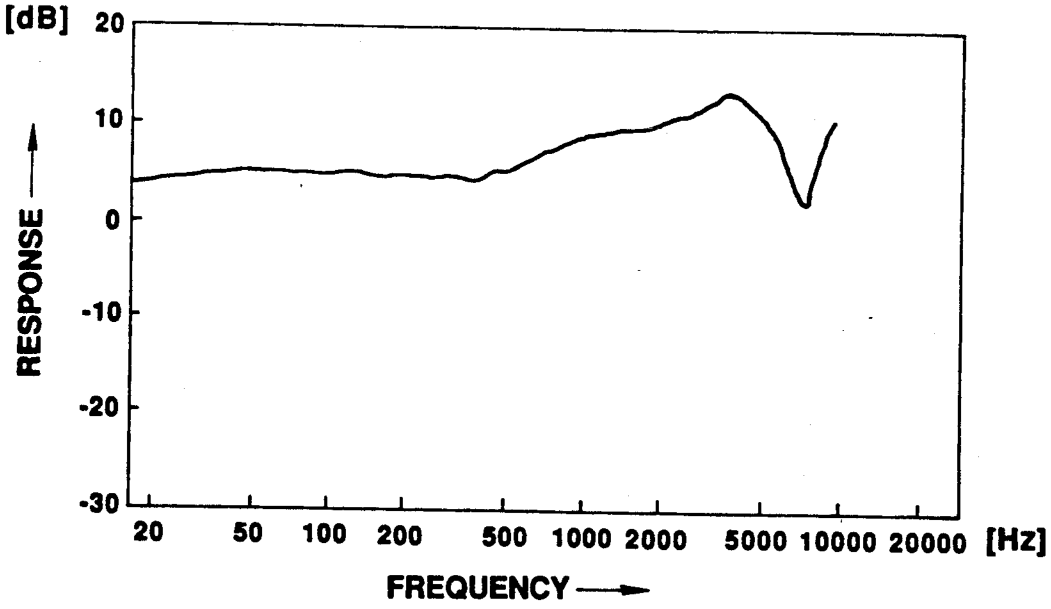
FIG. 5 is a chart showing output frequency characteristics of a microphone.
Figure 6:
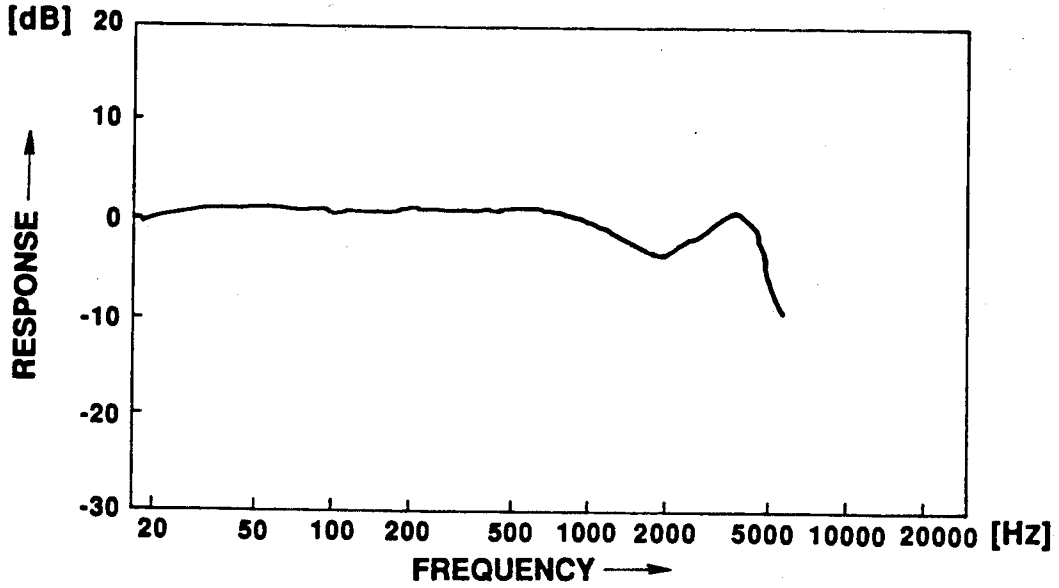
FIG. 6 is a chart showing the frequency ratio between the transfer function M of the microphone and the transfer function F of the acoustic characteristics block.

If the microphone 2 is provided in the vicinity of the acoustic meatus 22, as in the specific examples shown in FIGS. 2 and 3, the frequency characteristic M of the microphone 2 are approximately equal to the frequency characteristics F of the acoustic block 6 shown in FIG. 4 (F=M), as shown in FIG. 5, in which case $\beta \approx -1/AH$. That is, the ratio M/F between the frequency characteristics F and M is substantially flat up to around 1.5 kHz, as shown in FIG. 6, such that it becomes possible with the control circuit 3 having the characteristics $\beta$ to cancel the external noises reaching the acoustic meatus 22 by slightly correcting the transfer characteristics H of the sound producing means 5.

In the above description, the noise reducing device according to the present invention is applied to the inner ear type headphone device. However, the present invention may also be applied to an ear applying type headphone device. The frequency characteristics F of the acoustic block 6 are substantially not affected in the lower frequency range of not higher than around 1 kHz by an ear pad of the ear-applying type headphone device, so that, with the microphone provided in proximity to the acoustic meatus, the frequency characteristics F and M are about equal to each other, and hence the external noises may be cancelled by slightly correcting the transfer characteristics H of the headphone unit.

In the above embodiment, since the microphone as the acoustic-electrical transducer means is provided at a point of the sound producing means proximate to the acoustic meatus for picking up the external noises, while the acoustic signals having the same frequency spectrum as and reversed in phase with respect to the external noise reaching the acoustic meatus are produced by the sound producing means as electro-acoustic transducer means, the external noises may be reduced without inconveniences, such as oscillations, in distinction from the system in which the external noise is reduced by a negative feedback loop.

Also, when the noise reducing device is applied to the ear applying type headphone device, since there is no necessity of pressing a headphone cup to the lateral sides of the user's head to interrupt the external noises by the lateral pressure, the user may feel relaxed when wearing the headphone device for an extended period of time.

By referring to the drawings, the arrangement of using the above sound reducing device in listening to the audio signals is explained.

Figure 7:
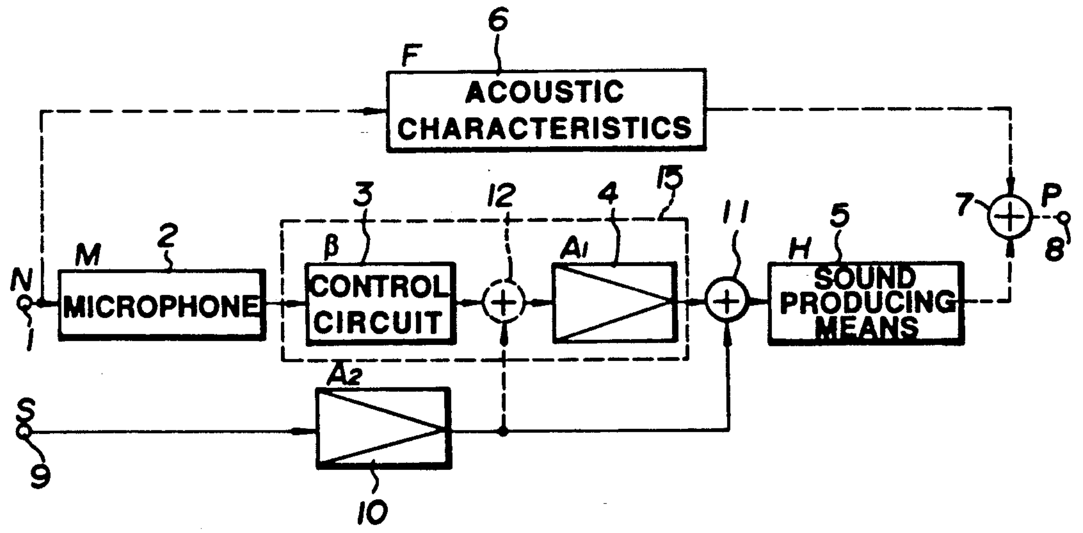
FIG. 7 is a block diagram showing an arrangement in which desired audible signals are heard with the use of the noise reducing device of the present invention.

FIG. 7 is a block diagram showing the basic arrangement for listening to audio signals. In this figure, parts or components similar to those used in FIG. 1 are designated by the same numerals and the detailed description is omitted for simplicity.

In FIG. 7, external noises of an acoustic nature are supplied to a microphone 2 as acoustic-electrical transducer means and thereby converted into electrical signals. The output signals from the microphone 2 are supplied to a control circuit 3 of characteristics transfer means 15 comprised of the control circuit 3 and an amplifier circuit 4. The output signals from the control circuit 3 are amplified by the amplifier circuit 4 and supplied to a summing point 11. To this summing point 11, there are also supplied external electrical audible signals via an input terminal 9 and an amplifier circuit 10. By these audible signals are meant voice or musical signals within the audio frequency range, such as the voice of a person from a ground station which is heard by aircraft pilots, the voice of a person over a telephone or audio playback signals from a sound reproducing system. The summing point 11 electrical sums the amplified output signal from the control circuit 3 and the above mentioned audible signal to supply the sum signal to sound producing means 5. The output signal from the amplifier circuits 4 and 10 via the summing point 11 is converted by the sound producing means 5 into acoustic signals. The acoustic signals thus produced by the sound producing means 5 are summed by summing means 7 to acoustic signals from acoustic block 6 and the resulting sum signal is supplied at an acoustic output terminal 8 placed at the acoustic meatus. The acoustic block 6 represents acoustic characteristics between the sound input terminal 1 and the sound output terminal 8. It is noted that an acoustic component of the sound signal produced by the sound producing means 5 corresponding to the output electrical signal of the amplifier circuit 4 is of the same frequency spectrum as and opposite in phase with respect to the external noise transmitted to the acoustic meatus 22 via block 6 and thus acts for cancelling the external noise. Hence, only the acoustic component corresponding to output electrical signals (audible signals) of the amplifier circuit 10 can be heard clearly.

More specifically, with the sound pressure N at the sound input terminal 1, the transfer function M of the microphone 2, the transfer function $\beta$ of the control circuit 3, the transfer function $A_1$ of the amplifier circuit 4, the transfer function H of the sound producing means 5, the input playback signal S at the input terminal 9, the transfer function $A_2$ of the amplifier circuit 10 and the transfer function F of the acoustic circuit 6, the sound pressure P at the sound output terminal 8 is represented by $$P = A_2HS + (F + A_1HM\beta)N$$

Wherein the transfer functions M, $\beta$, $A_1$, $A_2$, H and F are expressed in the frequency domain. For reducing the sound pressure P at the acoustic meatus 22 to zero, it suffices to reduce the coefficient of the sound pressure N of the external noises to zero. Hence it is sufficient if the transfer function $\beta$ of the control circuit 3 is such that $$F + A_1HM\beta = 0$$

$$\therefore = -F/A_1HM$$

If the microphone 2 is provided in the vicinity of the acoustic meatus 22, as in the specific examples shown in FIGS. 2 and 3, the frequency characteristics M of the microphone 2 are approximately equal to the frequency characteristics F of the acoustic block 6 shown in FIG. 4 (F=M), as shown in FIG. 5, in which case $\beta \approx -1/A_1H$. That is, the ratio M/F between the frequency characteristics F and M is substantially flat up to ca. 1.5 kHz, as shown in FIG. 6, such that it becomes possible with the control circuit 3 having the characteristics $\beta$ to cancel the external noises reaching the acoustic meatus 22 by slightly correcting the transfer characteristics H of the sound producing means 5. Hence, only the acoustic audible signals, that is playback signals, can be heard clearly by a simplified arrangement.

Meanwhile, the summing point 11 may also be provided ahead of the amplifier circuit 4, as suggested by an imaginary summing point 12.

When hearing the audible signals from a sound reproducing device, such as a portable tape recorder, with the use of the above described sound reducing device, only the audible signals, that is the acoustic playback signals, may be heard clearly from the portable headphone player without the need to raise the sound volume when the external noise is at a higher level.

Figure 8:
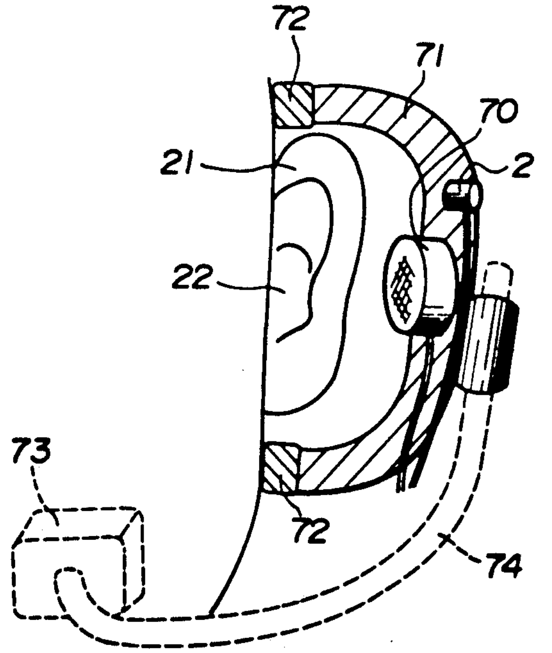
FIG. 8 is a cross-sectional view showing the state of use of the noise reducing device of the present invention, when applied to a head set.

FIG. 8 shows in cross-section the state of use of the noise reducing device of the present invention when applied to an ear-applying type headphone device or a so-called headset which is a trafficking or communication device used by an aircraft or helicopter pilot. In FIG. 8, parts or components similar to those of FIG. 7 are indicated by the same reference numerals, and a headphone unit 70 corresponds to the sound producing means 5 shown in FIG. 7.

With the headset shown in FIG. 8, a microphone 2 for picking up the external noises and the headphone unit 70 adapted for producing signals received from a control tower, for example, are enclosed in a headphone cup 71. An ear pad 72 is provided at a portion of the cup 71 contacting with the side portion of the wearer's head. A microphone 73 for transmission is attached to the end of a bar 74 attached to the outer side of the headphone cup 71.

The circuit construction of FIG. 8 is generally similar to that shown in FIG. 7. Thus, in FIGS. 7 and 8, the external noises, such as engine noises, are picked up by microphone 2 via sound input terminal 1 and converted into an electrical signal. On the other hand, an electrical signal of the same frequency spectrum as and opposite in phase with respect to the external noise reaching the acoustic meatus is produced by the control circuit 3 and supplied after amplification by the amplifier circuit 4 to the summing point 11 as a first electrical signal. To the summing point 11, there is also supplied a communication signal (voice signal) from, for example, a control tower, as a second electrical signal, via input terminal 9 and amplifier circuit 10. These first and second electrical signals are summed at the summing point 11 before being supplied to the headphone unit 70. The headphone unit produces acoustic signals converted from the second electrical signal, that is the communication signal from the control tower, while simultaneously producing acoustic signals converted from the first electrical signal which is controlled so as to be of the same frequency spectrum as and opposite in phase with respect to the external noise, such as the engine noise, reaching the acoustic meatus 22, during the time the electrical signal is transmitted from the microphone to the headphone unit 70. In this manner, the external noises are cancelled and only the audible signals, which are the communication signals, can be heard clearly.

Although the headset is provided with the ear pad 72, the effect of the ear pad 72 on the frequency characteristics F of the acoustic block 6 is practically nil at the low frequency range of not higher than about 1 kHz, such that, by providing the microphone 2 in the vicinity of the acoustic meatus 22, the frequency characteristics F, M are approximately equal to each other, as mentioned previously, and the external noises may be cancelled simply by inverting the phase of the external noise picked up by the control circuit 3 or by slightly correcting the transfer characteristics H of the headphone unit 6.

On the other hand, since there is no necessity of pressing the headphone cup, such as the ear pad 71, onto the side portion of the user's head for suppressing the external noise by the side pressure, the user can wear the headset for an extended time period with no disagreeable feeling.

Figure 9:
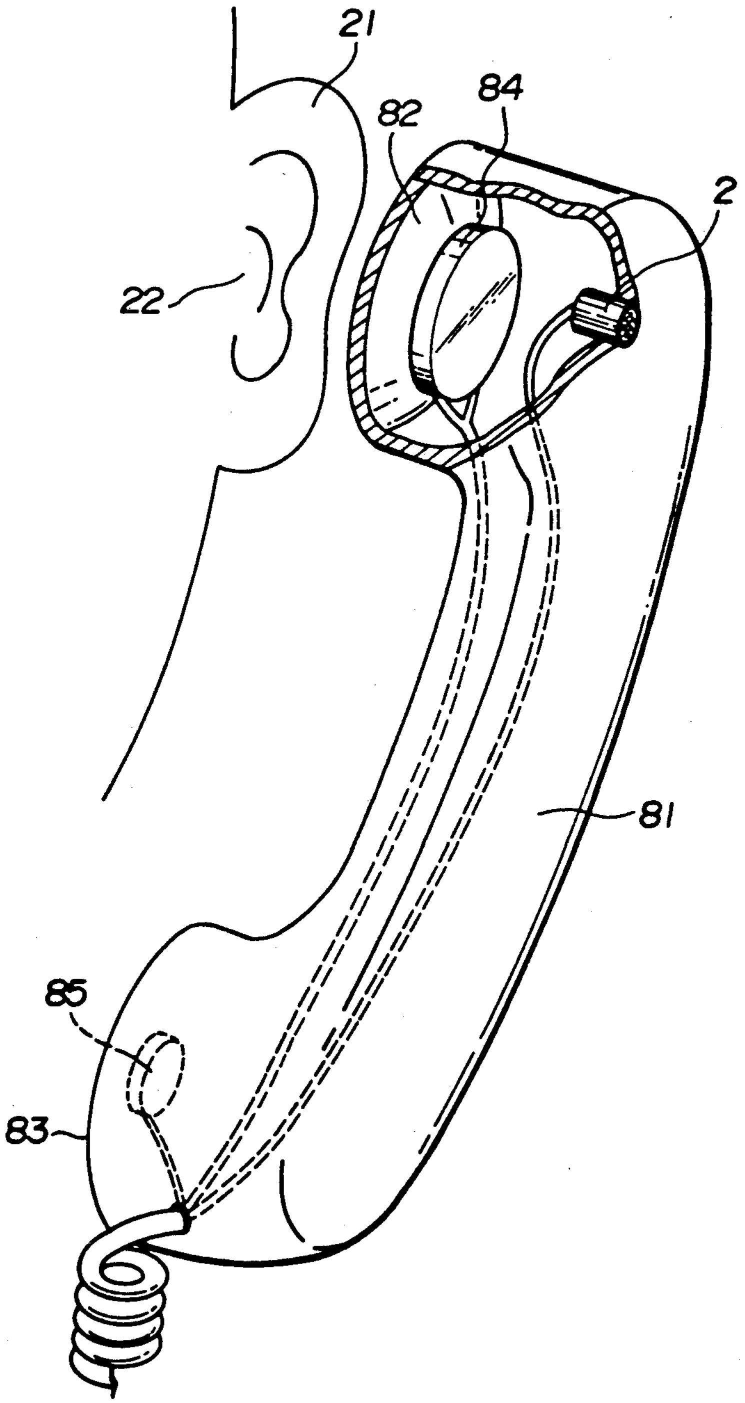
FIG. 9 is a perspective view, partially cut away, and showing the state of use of the noise reducing device of the present invention, when applied to a telephone handset.

FIG. 9 shows, in a perspective view, partially cut away, the state of use of the noise reducing device of the present invention, when applied to a telephone handset. In this figure, parts or components similar to those of FIG. 7 are denoted by the same reference numerals The sound producing means 5 shown in FIG. 7 corresponds to a speaker unit 84.

Referring to FIG. 9, the handset is provided with an ear piece 82 and a mouth piece 83 on both ends of a grip 81. The speaker unit 84 adapted for simultaneously producing the received voice signal and the acoustic signal of the same frequency spectrum as and opposite in phase with respect to the external noise as later described is enclosed within the ear piece 82, while a microphone 2 for picking up the external noise is enclosed in the grip 81 in the vicinity of the speaker unit 84. A microphone 85 for transmission is enclosed in the mouth piece 83.

The circuit construction of FIG. 9 is generally similar to that shown in FIG. 7. Thus, in FIGS. 7 and 9, the external noises are picked up by microphone 2 via sound input terminal 1 and converted into an electrical signal. On the other hand, an electrical signal of the same frequency spectrum as and opposite in phase with respect to the external noise reaching the acoustic meatus is produced by the control circuit 3 and supplied after amplification by the amplifier circuit 4 to the summing point 11 as a first electrical signal. To the summing point 11, there is also supplied a voice signal over a telephone as a second electrical signal, via input terminal 9 and amplifier circuit 10. These first and second electrical signals are summed at the summing point 11 before being supplied to the speaker unit 82 as the sound producing means 5 shown in FIG. 7. The speaker unit 82 produces acoustic signals converted from the second electrical signal, that is the communication signal from the control tower, while simultaneously producing acoustic signals converted from the first electrical signal which is controlled so as to be of the same frequency spectrum as and opposite in phase with respect to the external noise reaching the acoustic meatus 22, during the time the electrical signal is transmitted from the microphone to the headphone unit 70. In this manner, the external noises are cancelled and only the audible signals, which are the communication signals, can be heard clearly.

By providing the microphone 2 in the vicinity of the acoustic meatus 22, the frequency characteristics F and M may be approximately equal to each other and the external noises may be cancelled only by slightly modifying the transfer characteristics H of the speaker unit 84.

In this manner, by applying the noise reducing device of the present invention to the telephone handset, one may talk over the telephone without being bothered by external noises.

The noise reducing device according to the present invention is not limited to the above described illustrative embodiment, but may be easily applied to transceivers or helmets fitted with a headphone which is employed under high noise environments, such as construction sites.

Meanwhile, with the above described noise reducing device, when the external noise is reduced with the high noise reduction level, the wearer may feel his or her ears "stopped" or "clogged" and thus may feel disagreeable. When the device is set to a lower noise reduction level, the "stopped" feeling may be avoided, however, the device may not be conveniently employed under high noise environment, such as in cockpits or construction sites.

Thus a noise reducing device is desired in which a high noise reduction level may be achieved under high noise conditions and, when the external noise is reduced, the noise reduction level is lowered to avoid the situation in which the wearer feels his or her ears "stopped".

Figure 10:
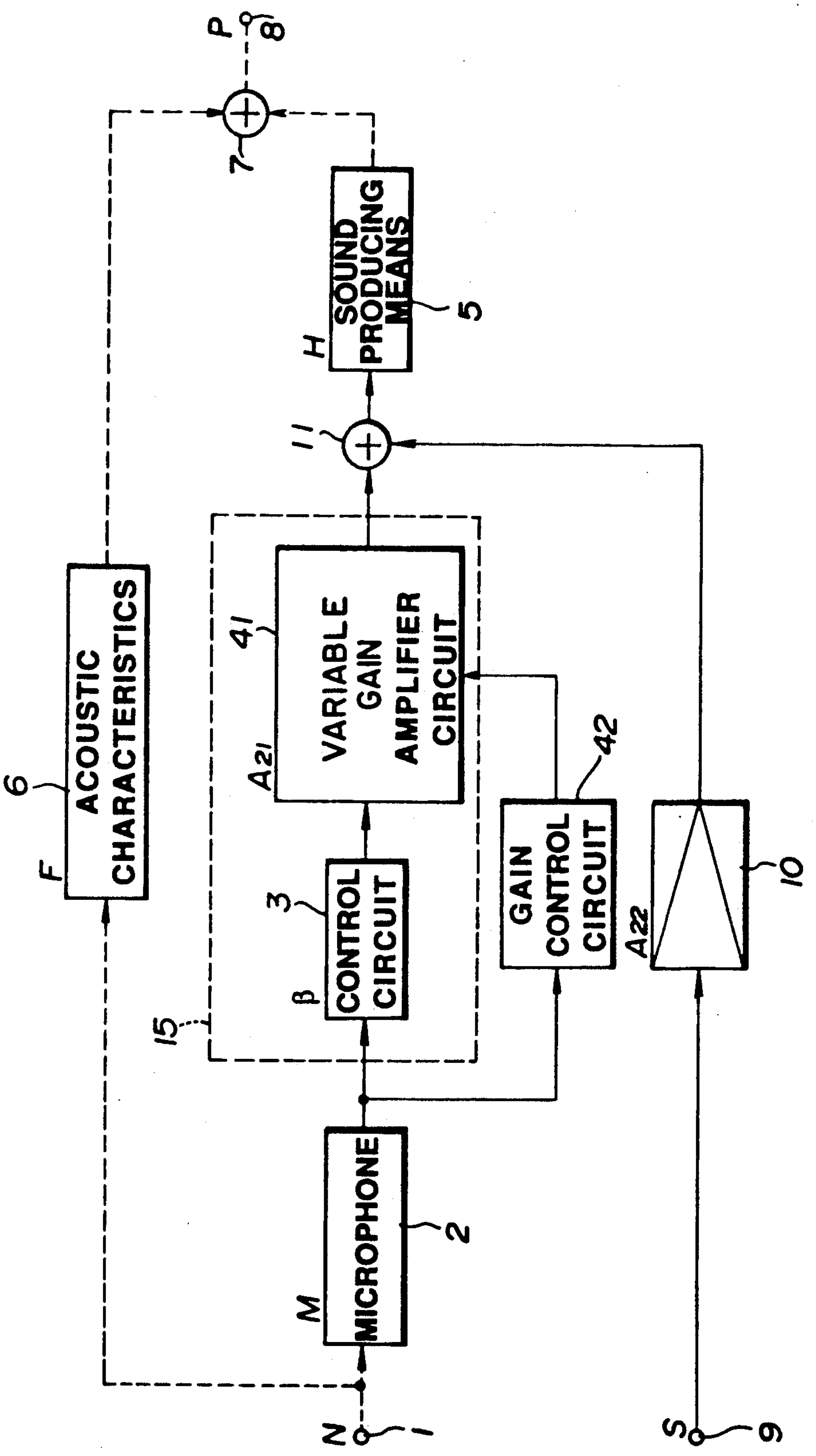
FIG. 10 is a block diagram showing a modified embodiment of a noise reducing device according to the present invention.

FIG. 10 shows, in a block diagram, a modifi-·¹ embodiment of the noise reducing device according to the present invention.

Referring to FIG. 10, external noises of an acoustic nature are input at a sound input terminal 1 and thence transmitted to a microphone 2 as acoustic-electrical transducer means so as to be converted into electrical signals. The output signal from the microphone 2 is supplied to transfer means 15 consisting of a control circuit 3 and a variable gain amplifier circuit 41. The gain or amplification factor of the variable gain amplifier circuit 41 within the transfer means 15 is varied as a function of a control signal which is input to the circuit 41 from a gain control circuit 42 adapted for detecting the level, such as the effective value, of the external noise of the output signal from microphone 2. The gain control circuit 42 outputs the control signal which will increase the gain or amplification factor of the circuit 41 for a higher detected noise level and which conversely will lower the gain of the circuit 41 for a lower detected noise level. The output signal from the transfer means 15 is supplied as the first electrical signal to the summation point 11. To this summation point 11, there is also supplied a playback signal from outside, such as playback signal from a portable sound reproducing apparatus, as the second electrical signal, via input terminal 9 and an amplifier circuit 10. The summing point 11 electrically sums the first electrical signal, that is the output signal from the transmission means 15, and the second electrical signal, that is the above mentioned playback signal, to transmit the sum signal to sound producing means 5. The sound producing means converts the signal supplied from the summing point 11 to produce acoustic signals converted from the electrical signals. The produced acoustic signals are acoustically summed at the summation point 7 to acoustic signals from the acoustic block 6 so as to be supplied to the acoustic output terminal 8 placed at the user's acoustic meatus.

With the above described embodiment, since the external noise reduction level is not excessively increased for the lower external noise level, the sense of "stopped" ear as mentioned previously may be eliminated and the user may hear the reproduced acoustic signals, converted from the second electrical signals, under a moderate noise reducing level which may be controlled as a function of the external noise level.

More specifically, with the sound pressure N at the sound input terminal 1, the transfer function M of the microphone *2*, the transfer function $\beta$ of the control circuit 3, the transfer function $A_{21}$ of the amplifier circuit or the variable gain amplifier circuit 41, the transfer function $A_{22}$ of the amplifier circuit 10, the transfer function H of the sound producing means 5 and the transfer function F of the acoustic block 6, the sound pressure P at the sound output terminal 8 may be expressed by $$P = A_{22}HS + (F + A_{21}HM\beta)N$$

wherein the transfer functions M, $\beta$, $A_{21}$, $A_{22}$, H and F are expressed in the frequency domain. It is seen from the above formula that the external noise N may be changed without regard to the signal component S by changing the transfer function $A_{21}$ of the amplifier circuit 41. It is noted that, for reducing the sound pressure P in the acoustic meatus 22 to zero, it suffices to reduce the coefficient of the sound pressure of the external noise N to zero. Thus, as a principle, by setting the transfer function $\beta$ of the control circuit 3 so that $$0 = F + A_{21}HM\beta$$

and hence $\beta = -F/A_{21}HM$ the noise may be reduced to zero. Since the gain or transfer function $A_{21}$ of the amplifier circuit 41 is variable and the transfer function $\beta$ of the control circuit 3 is fixed, the formula of transfer function $\beta$ may be rewritten, using a fixed value $A_{IF}$ in view of $A_{21}$ to $$\beta = -F/A_{IF}HM$$

such that the sound pressure P at the sound output terminal 13 is given by $$P = A_{22}HS + \left(F + \frac{-FA_{21}HM}{A_{IF}HM}\right)N$$

$$= A_{22}H_S + F(1 - (A_{21}/A_{IF}))N$$

In the above formula, if the gain $A_{21}$ of the amplifier circuit 41 is controlled so as to be increased or decreased within the range of not higher than $A_{IF}$, the term of the external noise N in the above formula approaches to zero as the value of $A_{21}$ is increased from a lower value to approach to $A_{IF}$, so that the gain $A_{21}$ of the variable gain amplifier circuit 41 is controlled so as to be smaller with the lower level of the external noise to eliminate the sense of "stopped" ear.

What is claimed is:

1. A noise reducing device in which an external noise reaching a user's acoustic meatus may be reduced by being acoustically combined with an acoustic signal output by an electro-acoustic transducer arranged facing a user's acoustic meatus when the noise reducing device is worn a user, comprising:

acoustic-electrical transducer means arranged in a direction away from the user's acoustic meatus and in the vicinity of said electro-acoustic transducer that faces toward the user's acoustic meatus for picking up the external noise exclusive of the output of the said electro-acoustic transducer and producing an output signal therefrom, characteristics transfer means having predetermined phase and frequency transfer characteristics matched to acoustic frequency characteristics of the external noise for receiving said output signal form said acoustic-electrical transducer means and supplying an output signal to said electro-acoustic transducer that produces an acoustic signal therefrom, said characteristics transfer means including control means receiving said output signal from said acoustic-electrical transducer means for producing a phase-inverted output signal therefrom, and amplifier means having a variable gain for amplifying said phase-inverted output signal from said control means and supplying an amplified, phase-inverted signal to said electro-acoustic transducer, wherein the phase and frequency transfer characteristic of said characteristics transfer means are predetermined so that the transfer characteristics from said acoustic-electrical transducer means to said electro-acoustic transducer means are in registry with and opposite in phase to acoustic frequency characteristics of the external noise, and further comprising gain control means for detecting the output signal level of said acoustic-electrical transducer means and controlling the gain of said amplifier means in said characteristics transfer means in response thereto.

2. The device according to claim 1, wherein said gain control means performs a control operation so that the gain of said amplifier means is increased for a higher output signal level of said acoustic-electrical transducer means detected by said gain control means and so that the gain of said amplifier means is decreased for a lower output signal level of said acoustic-electrical transducer means detected by said gain control means.

3. The device according to claim 1 wherein said acoustic-electrical transducer means has a transfer function M, said control means has a transfer function $\beta$, said amplifier means has a transfer function A, said electro-acoustic transducer has a transfer function H, and the external noise input to said acoustic-electrical transducer means has acoustic characteristics F, and the transfer characteristics of said control means are predetermined so that the relation $\beta = -F/AHM$ is satisfied.

4. The device according to claim 1, wherein said control means has a transfer function $\beta$, said amplifier means has a transfer function A, and said electro-acoustic transducer means has a transfer function H, the transfer characteristics of said control means are predetermined so that the relation $\beta = -1/AH$ is satisfied.

5. A noise reducing device in which an external noise reaching a user's acoustic meatus may be reduced by an acoustic signal output by an electro-acoustic transducer arranged in the vicinity of the user's ear when the noise reducing device is worn by the user, comprising:

acoustic-electrical transducer means arranged in the vicinity of said electro-acoustic transducer means and directed in a direction away from the user's acoustic means and adapted to pick up the external noise in the vicinity of the user's ear exclusive of the output of electro-acoustic transducer, control means supplied with the output of said acoustic-electrical transducer means for controlling the transfer characteristics of a signal input thereto by having predetermined phase and frequency transfer characteristics matched to acoustic frequency characteristics of the external noise and producing an output signal, amplifier means having a variable gain for amplifying the output signal of said control means and supplying an amplified output signal to said electro-acoustic transducer, signal summing means for summing an audio program signal for reproduction by said electro-acoustic transducer and said amplified output signal from said amplifier means and producing a summed signal fed to and input of said electro-acoustic transducer, wherein the transfer characteristics of said control means are predetermined so that the transfer characteristics from said acoustic-electrical transducer means to said electro-acoustic transducer are in registry with and opposite in phase to the acoustic frequency characteristics of the external noise reaching the user's acoustic meatus, and the acoustic signal from the electro-acoustic transducer and the external noise are acoustically combined in the vicinity of the user's acoustic meatus, and further comprising gain control means for detecting the output signal level of said acoustic-electrical transducer means and controlling the gain of said amplifier means in response thereto.

6. The device according to claim 5, wherein said acoustic-electrical transducer means has as a transfer function M, said control means has a transfer function $\beta$, said amplifier means has a transfer function A, said electro-acoustic transducer has a transfer function H, and the external noise has acoustic characteristics F, the transfer characteristics of said control means are predetermined so that the relation $\beta = -F/AHM$ is satisfied.

7. The device according to claim 5, wherein said gain control means performs a control operation so that the gain of said amplifier means is increased for a higher output signal level of said acoustic-electrical transducer means detected by said gain control means and so that the gain of said amplifier means is decreased for a lower output signal level of said acoustic-electrical transducer means detected by said gain control means.

8. The device according to claim 5, wherein said control means has a transfer function $\beta$, said amplifier means has a transfer function A, and said electro-acoustic transducer has a transfer function H, and transfer characteristics of said control means are predetermined so that the relation $\beta = -1/AH$ is satisfied.

* * * * *